United States Patent
Daniëls et al.

(10) Patent No.: US 10,654,767 B2
(45) Date of Patent: May 19, 2020

(54) PROCESS FOR PRODUCING ALKYLATED AROMATIC HYDROCARBONS FROM A MIXED HYDROCARBON FEEDSTREAM

(71) Applicant: SABIC GLOBAL TECHNOLOGIES B.V., Bergen op Zoom (NL)

(72) Inventors: Dimitri Daniëls, Geleen (NL); Kae Shin Wong, Geleen (NL)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/321,352

(22) PCT Filed: Jun. 25, 2015

(86) PCT No.: PCT/EP2015/064315
§ 371 (c)(1),
(2) Date: Dec. 22, 2016

(87) PCT Pub. No.: WO2015/197733
PCT Pub. Date: Dec. 30, 2015

(65) Prior Publication Data
US 2017/0144946 A1   May 25, 2017

(30) Foreign Application Priority Data

Jun. 26, 2014 (EP) ..................... 14174371

(51) Int. Cl.
| | |
|---|---|
| C07C 2/66 | (2006.01) |
| C10G 47/16 | (2006.01) |
| C07C 4/06 | (2006.01) |
| C10G 69/00 | (2006.01) |
| C10G 69/12 | (2006.01) |
| C10G 29/20 | (2006.01) |
| C10G 9/00 | (2006.01) |
| C07C 5/333 | (2006.01) |

(52) U.S. Cl.
CPC ............ C07C 2/66 (2013.01); C07C 4/06 (2013.01); C07C 5/333 (2013.01); C10G 9/00 (2013.01); C10G 29/205 (2013.01); C10G 47/16 (2013.01); C10G 69/00 (2013.01); C10G 69/123 (2013.01); C07C 2521/04 (2013.01); C07C 2523/42 (2013.01); C07C 2529/40 (2013.01); C07C 2529/44 (2013.01)

(58) Field of Classification Search
CPC ............ C07C 4/00–26; C10G 47/00–36
See application file for complete search history.

(56) References Cited

U.S. PATENT DOCUMENTS

| | | | |
|---|---|---|---|
| 2,898,387 A | 8/1959 | Teter | |
| 3,027,413 A | 3/1962 | Moy et al. | |
| 3,639,495 A | 2/1972 | Brewer et al. | |
| 3,770,614 A * | 11/1973 | Graven | B01J 29/40 208/62 |
| 4,056,575 A | 11/1977 | Gregory et al. | |
| 4,157,356 A | 6/1979 | Bulford et al. | |
| 4,180,689 A | 12/1979 | Davies et al. | |
| 4,190,519 A | 2/1980 | Miller et al. | |
| 4,358,364 A | 11/1982 | Klosek et al. | |
| 4,456,527 A | 6/1984 | Buss et al. | |
| 4,503,023 A * | 3/1985 | Breck | B01J 29/06 423/715 |
| 4,827,072 A | 5/1989 | Imai et al. | |
| 4,926,005 A | 5/1990 | Olbrich et al. | |
| 5,189,234 A * | 2/1993 | Amelse | C07C 5/325 585/320 |
| 5,401,386 A | 3/1995 | Morrison et al. | |
| 6,177,600 B1 | 1/2001 | Netzer | |
| 7,259,282 B2 * | 8/2007 | Hildreth | C07C 2/64 585/446 |
| 7,772,448 B2 * | 8/2010 | Clark | C07C 2/66 585/449 |
| 8,258,360 B2 | 9/2012 | Clark et al. | |
| 8,309,778 B2 * | 11/2012 | Wang | B01J 29/068 208/137 |
| 2005/0194289 A1 | 9/2005 | Overbeek et al. | |
| 2008/0255398 A1 | 10/2008 | Stevenson et al. | |
| 2008/0293990 A1 | 11/2008 | Stevenson et al. | |
| 2011/0132804 A1 | 6/2011 | Stevenson et al. | |
| 2012/0149958 A1 | 6/2012 | Ellrich et al. | |
| 2013/0338410 A1 | 12/2013 | Wang et al. | |
| 2017/0144948 A1 | 5/2017 | Stevenson et al. | |

FOREIGN PATENT DOCUMENTS

| | | |
|---|---|---|
| CN | 1098084 A | 2/1995 |
| CN | 101151351 A | 3/2008 |
| CN | 101679141 A | 3/2010 |

(Continued)

OTHER PUBLICATIONS

Alfke et al., "Oil Refining", Ullmann's Encyclopedia of Industrial Chemistry, 2007, 55 pages.
Hwang, et al., "Cumene—Kirk Othmer Encyclopedia of Chemical Technology", 2010, pp. 1-10.
International Search Report for International Application No. PCT/EP2015/064315; dated Sep. 15, 2015; 4 Pages.
Laredo et al., "Benzene reduction in gasoline by alkylation with olefins: Effect of the feedstock on the catalyst deactivation", Catalysis A: General, 2009, vol. 363, pp. 11-18.

(Continued)

Primary Examiner — In Suk C Bullock
Assistant Examiner — Alyssa L Cepluch
(74) Attorney, Agent, or Firm — Cantor Colburn LLP

(57) ABSTRACT

The present invention relates to a process for producing alkylated aromatic hydrocarbons such as ethyl benzene or cumene from a mixed hydrocarbon feedstream comprising subjecting C6 cut separated from said mixed hydrocarbon feedstream to hydrocracking to provide benzene and subjecting said benzene to alkylation.

19 Claims, No Drawings

(56) References Cited

FOREIGN PATENT DOCUMENTS

| EP | 0192059 A1 | 8/1986 | |
|---|---|---|---|
| GB | 2162082 A | 1/1986 | |
| WO | WO-9400409 A1 * | 1/1994 | ............. C10G 29/16 |
| WO | 0244306 A1 | 6/2002 | |
| WO | 2004013095 A2 | 2/2004 | |
| WO | 2005085157 A1 | 9/2005 | |
| WO | 2007055488 A1 | 5/2007 | |
| WO | 2013182534 A1 | 12/2013 | |

OTHER PUBLICATIONS

Laredo et al., "Benzene reduction in gasoline by olefin alkylation: Effect of the catalyst on a C6-reformate heart-cut", Catalysis A: General, 2009, vol. 363, pp. 19-26.

Vora et al., "Alkylation—Kirk Othmer Encyclopedia of Chemical Technology", 2003, vol. 2, 35 pages.

Written Opinion of the International Search Report for International Application No. PCT/EP2015/064315; dated Sep. 15, 2015; 6 Pages.

"Safety Data Sheet Naphtha", Holly Frontier, Jul. 25, 2014, pp. 1-14.

Encyclopaedia of Hydrocarbons, "Aromatics: Aromatics production and use", 2006, vol. II, Refining and Petrochemicals, Chapter 10.6, pp. 591-614.

Nagamori et al., "Converting light hydrocarbons containing olefins to aromatics (Alpha Process)", Microporous and Mesoporous Materials, 1998, vol. 21, pp. 439-445.

* cited by examiner

PROCESS FOR PRODUCING ALKYLATED AROMATIC HYDROCARBONS FROM A MIXED HYDROCARBON FEEDSTREAM

CROSS REFERENCE TO RELATED APPLICATIONS

This application is a 371 of International Application No. PCT/EP2015/064315, filed Jun. 25, 2015, which claims priority to European Application No. 14174371.6 filed Jun. 26, 2014, both of which are incorporated herein by reference in their entirety.

The present invention relates to a process for producing alkylated aromatic hydrocarbons such as ethyl benzene or cumene from a mixed hydrocarbon feedstream comprising subjecting C6 cut separated from said mixed hydrocarbon feedstream to hydrocracking to provide benzene and subjecting said benzene to alkylation.

The commercial production of the benzene derivatives ethylbenzene ("EB") or cumene comprises the alkylation of benzene using ethylene or propylene as alkylation agent; see e.g. Hwang and Chen (2010) Cumene Kirk-Othmer Encyclopedia of Chemical Technology 1-10. Direct alkylation of a mixed C6 hydrocarbon feedstream is not a viable method to produce high-purity ethylbenzene or cumene since in such a process many undesired by-products are produced which are difficult to separate from the desired aromatic alkylation products; see e.g. U.S. Pat. No. 6,177,600. Therefore, a mixed hydrocarbon feedstream such as reformate or C6 cut conventionally needs to be subjected to aromatic extraction, such as liquid extraction or extractive distillation, to remove the benzene co-boilers in order to provide a sufficiently purified benzene stream. A drawback of such a process for producing benzene is that aromatic extraction methods are expensive and time consuming.

It was an object of the present invention to provide an improved process for producing high-purity alkylated aromatic hydrocarbons from a mixed hydrocarbon feed.

The solution to the above problem is achieved by providing the embodiments as described herein below and as characterized in the claims. Accordingly, the present invention provides a process for producing alkylated aromatic hydrocarbons comprising:

(a) subjecting a mixed hydrocarbon feedstream to a separation to provide a C6 cut;
(b) subjecting C6 cut to hydrocracking to provide benzene;
(c) subjecting benzene to alkylation to provide a product stream rich in alkylated aromatic hydrocarbons.

In the context of the present invention, it was surprisingly found that by using the process of the present invention, the yield of highly desired aromatic compounds such as benzene and cumene can be dramatically increased when compared to the conventional aromatic alkylation process, which mainly produces the less desired C6 paraffins. Furthermore, benzene having a purity of more than 99 wt-% can be produced from alkylate without need of extraction. Moreover, it was found that in the process of the present invention the alkylation reactor can be smaller and more efficient when compared to a process wherein a feed comprising benzene diluted with other hydrocarbons is subjected to alkylation.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

As used herein, the term "C # hydrocarbons", or "C #", wherein "#" is a positive integer, is meant to describe all hydrocarbons having # carbon atoms. Moreover, the term "C #+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms. The term "C2-3 alkane" accordingly relates to alkanes having 2 or 3 carbon atoms. The term "C2-3 alkene" accordingly relates to alkenes having 2 or 3 carbon atoms.

In the process of the present invention, any mixed hydrocarbon composition that comprises C6 hydrocarbons and that is suitable to be subjected to hydrocracking to provide a benzene stream can be used as a feedstream. Such a suitable feedstream may be selected from the group consisting of reformate, C6 cut, straight run naphtha, hydrocracked gasoline, light coker naphtha, coke oven light oil and FCC gasoline, or mixtures thereof.

It is an advantage of the present invention that feedstream subjected to hydrocracking may comprise relatively high amounts of sulfur. For instance, the feedstream used in the process of the present invention may comprise up to 300 wppm of sulfur (i.e. the weight of sulfur atoms, present in any compound, in relation to the total weight of the feed). It is an advantage of the process of the present invention that it is not necessary to subject the hydrocarbon feedstream to a desulfurisation treatment prior to subjecting said hydrocarbon feedstream to the hydrocracking treatment. Preferably, the feedstream comprises 10-300 wppm of sulfur wherein the benzene product stream produced by hydrocracking comprises 0.1-5 wppm of sulfur. Methods for the measurement of the sulfur content in a hydrocarbons stream are well-well known. Preferably, the sulfur content is measured using the IP 490 standard; see also ISO 20846:2011. Accordingly, samples are introduced into a pyrolysis furnace, where the sample is oxidized at high temperature in an oxygen atmosphere. All sulphur in the sample is oxidized to $SO_2$. The $SO_2$ is exposed to ultraviolet light, causing it to fluoresce. The light emitted by the fluorescence is detected by a photomultiplier, and the resulting signal is proportional to the sulfur content of the sample. Preferably, the feedstream comprises reformate.

The process of the present invention comprises subjecting a mixed hydrocarbon feedstream to a separation to provide a C6 cut. As used herein, the term "C6 cut" relates to a hydrocarbon fraction comprising at least 60 wt-% C6 hydrocarbons, preferably at least at least 70 wt-% C6 hydrocarbons, more preferably at least 80 wt-% C6 hydrocarbons, particularly preferably at least 90 wt-% C6 hydrocarbons, more particularly preferably at least 95 wt-% C6 hydrocarbons, and most preferably at least 99 wt-% C6 hydrocarbons. Preferably, the separation to provide a C6 cut does not involve aromatic extraction, such as liquid extraction or extractive distillation. Preferably, the separation to provide a C6 cut involves distillation. The skilled person is capable of selecting the suitable distillation conditions to provide a C6 cut as defined herein. Preferably, the distillation conditions are suitable to provide a C6 cut having a boiling point range of 45-95° C., more preferably of 47-90° C., particularly preferably of 48-85° C. and most preferably 49-81° C. The hydrocarbons comprised in the mixed hydrocarbon feedstream and which are not comprised in the C6 cut, such as the C7+ cut, may be subjected to further chemical processing or separation or may be used as such. Preferably, the C7+ cut is added to the gasoline blending pool.

Accordingly, the process of the present invention may involve hydrocracking, which comprises contacting the benzene-rich aromatic stream in the presence of hydrogen with a hydrocracking catalyst under hydrocracking conditions. The process conditions useful hydrocracking, also described herein as "hydrocracking conditions", can be easily determined by the person skilled in the art; see e.g. (2007) Oil Refining, Ullmann's Encyclopedia of Industrial Chemistry.

The term "hydrocracking" is used herein in its generally accepted sense and thus may be defined as a catalytic cracking process assisted by the presence of an elevated partial pressure of hydrogen; see e.g. Alfke et al. (2007) loc.cit. The products of the hydrocracking process step are LPG and benzene. The process conditions used for hydrocracking generally includes a process temperature of 200-600° C., elevated pressures of 0.2-20 MPa, space velocities between 0.1-20 $h^{-1}$. Hydrocracking reactions proceed through a bifunctional mechanism which requires an acid function, which provides for the cracking and isomerization and which provides breaking and/or rearrangement of the carbon-carbon bonds comprised in the hydrocarbon compounds comprised in the feed, and a hydrogenation function. Many catalysts used for the hydrocracking process are formed by combining various transition metals, or metal sulfides with the solid support such as alumina, silica, alumina-silica, magnesia and zeolites.

Preferably the benzene is recovered from benzene-rich aromatic stream by subjecting said benzene-rich aromatic stream to gasoline hydrocracking. As used herein, the term "gasoline hydrocracking" or "GHC" refers to a hydrocracking process that is particularly suitable for converting a complex hydrocarbon feed that is relatively rich in aromatic hydrocarbon compounds—such as benzene-rich aromatic stream obtained in the process of the present invention—to LPG and benzene, wherein said process is optimized to keep one aromatic ring intact of the aromatics comprised in the GHC feedstream, but to remove most of the side-chains from said aromatic ring. Accordingly, the main product produced by gasoline hydrocracking is benzene and the process can be optimized to provide chemicals-grade benzene. Preferably, the gasoline hydrocracking conditions include a temperature of 300-580° C., more preferably of 400-580° C. and even more preferably of 430-530° C. Lower temperatures must be avoided since hydrogenation of the aromatic ring becomes favourable, unless a specifically adapted hydrocracking catalyst is employed. For instance, in case the catalyst comprises a further element that reduces the hydrogenation activity of the catalyst, such as tin, lead or bismuth, lower temperatures may be selected for gasoline hydrocracking; see e.g. WO 02/44306 A1 and WO 2007/055488. In case the reaction temperature is too high, the yield of LPG's (especially propane and butanes) declines and the yield of methane rises. As the catalyst activity may decline over the lifetime of the catalyst, it is advantageous to increase the reactor temperature gradually over the lifetime of the catalyst to maintain the hydrocracking conversion rate. This means that the optimum temperature at the start of an operating cycle preferably is at the lower end of the hydrocracking temperature range. The optimum reactor temperature will rise as the catalyst deactivates so that at the end of a cycle (shortly before the catalyst is replaced or regenerated) the temperature preferably is selected at the higher end of the hydrocracking temperature range.

Preferably, the gasoline hydrocracking of the benzene-rich aromatic stream is performed at a pressure of 0.3-5 MPa gauge, more preferably at a pressure of 0.6-3 MPa gauge, particularly preferably at a pressure of 1-2 MPa gauge and most preferably at a pressure of 1.2-1.6 MPa gauge. By increasing reactor pressure, conversion of C5+ non-aromatics can be increased, but this also increases the yield of methane and the hydrogenation of aromatic rings to cyclohexane species which can be cracked to LPG species. This results in a reduction in benzene yield as the pressure is increased and, as some cyclohexane and its isomer methylcyclopentane, are not fully hydrocracked, there is an optimum in the purity of the resultant benzene at a pressure of 1.2-1.6 MPa.

Preferably, gasoline hydrocracking of a hydrocarbon feedstream is performed at a Weight Hourly Space Velocity (WHSV) of 0.1-20 $h^{-1}$, more preferably at a Weight Hourly Space Velocity of 0.2-15 $h^{-1}$ and most preferably at a Weight Hourly Space Velocity of 0.4-10 $h^{-1}$. When the space velocity is too high, not all benzene co-boiling paraffin components are hydrocracked, so it will not be possible to achieve benzene specification by simple distillation of the reactor product. At too low space velocity the yield of methane rises at the expense of propane and butane. By selecting the optimal Weight Hourly Space Velocity, it was surprisingly found that sufficiently complete reaction of the benzene co-boilers is achieved to produce on spec benzene without the need for a liquid recycle.

Preferably, the hydrocracking comprises contacting the benzene-rich aromatic stream in the presence of hydrogen with a hydrocracking catalyst under hydrocracking conditions, wherein the hydrocracking catalyst comprises 0.1-1 wt-% hydrogenation metal in relation to the total catalyst weight and a zeolite having a pore size of 5-8 Å and a silica ($SiO_2$) to alumina ($Al_2O_3$) molar ratio of 5-200 and wherein the hydrocracking conditions comprise a temperature of 400-580° C., a pressure of 300-5000 kPa gauge and a Weight Hourly Space Velocity (WHSV) of 0.1-20 $h^{-1}$. The hydrogenation metal preferably is at least one element selected from Group 10 of the periodic table of Elements, most preferably Pt. The zeolite preferably is MFI. Preferably a temperature of 420-550° C., a pressure of 600-3000 kPa gauge and a Weight Hourly Space Velocity of 0.2-15 $h^{-1}$ and more preferably a temperature of 430-530° C., a pressure of 1000-2000 kPa gauge and a Weight Hourly Space Velocity of 0.4-10 $h^{-1}$ is used.

Accordingly, preferred gasoline hydrocracking conditions thus include a temperature of 400-580° C., a pressure of 0.3-5 MPa gauge and a Weight Hourly Space Velocity of 0.1-20 $h^{-1}$. More preferred gasoline hydrocracking conditions include a temperature of 420-550° C., a pressure of 0.6-3 MPa gauge and a Weight Hourly Space Velocity of 0.2-15 $h^{-1}$. Particularly preferred gasoline hydrocracking conditions include a temperature of 430-530° C., a pressure of 1-2 MPa gauge and a Weight Hourly Space Velocity of 0.4-10 $h^{-1}$.

Accordingly, the hydrocracking preferably comprises contacting the benzene-rich aromatic stream in the presence of hydrogen with a hydrocracking catalyst under hydrocracking conditions.

The hydrocracking catalyst preferably comprises 0.1-1 wt-% hydrogenation metal in relation to the total catalyst weight and a zeolite having a pore size of 5-8 Å and a silica ($SiO_2$) to alumina ($Al_2O_3$) molar ratio of 5-200.

The hydrocracking conditions preferably comprise a temperature of 450-580° C., a pressure of 300-5000 kPa gauge and a Weight Hourly Space Velocity (WHSV) of 0.1-20 $h^{-1}$.

In the process of the present invention, accordingly, the hydrocracking produces a product stream comprising benzene and C1-C4 hydrocarbons. Preferably, the product stream produced by hydrocracking produces less than 5 wt-% of co-boilers of benzene, more preferably less than 2 wt-% co-boilers of benzene, particularly preferably less than 1 wt-% co-boilers of benzene and most preferably less than 0.2 wt-% co-boilers of benzene.

The benzene stream obtained by the hydrocracking step comprised in the process of the present invention preferably comprises at least 95 wt-% benzene, more preferably at least 98 wt-% benzene, particularly preferably at least 99 wt-% benzene and most preferably at least 99.8 wt-% benzene.

Preferably, wherein the benzene is preferably separated from the C1-C4 hydrocarbons by vapor-liquid separation.

Preferably, the separation to provide benzene does not involve aromatic extraction, such as liquid extraction or extractive distillation. The benzene is preferably separated from the other compounds comprised in the hydrocracking product using a flash vessel.

Accordingly, the process of the present invention involves alkylation, which comprises contacting the benzene with an alkylation agent in the presence of an alkylation catalyst under alkylation conditions. The process conditions useful alkylation, also described herein as "alkylation conditions", can be easily determined by the person skilled in the art; see e.g. Vora et al. (2003) Alkylation Kirk-Othmer Encyclopedia of Chemical Technology and Hwang and Chen (2010) loc. cit. The process conditions used for alkylation generally includes a process temperature of 100-300° C., a pressure of 0.5-10 MPa, a weight hourly space velocity of 0.5-20 h$^{-1}$ and benzene/alkylation agent molar ratio of 3-10. The benzene alkylation process step uses an acidic catalyst which may be a solid phosphoric acid catalyst (phosphoric acid supported on alumina) or an aluminum chloride complex as the catalyst or an acidic zeolite-based catalyst. Preferably, the zeolite comprised in the alkylation catalyst has a pore size of 6-8 Å. The optimal process conditions depend on the alkylation agent. For instance, when selecting propylene as the alkylation agent the process conditions are somewhat milder when compared to selecting ethylene as the alkylation agent.

The alkylation preferably comprises contacting the benzene in the presence of ethylene with an alkylation catalyst under alkylation conditions to produce ethylbenzene, wherein said alkylation catalyst comprises beta zeolite, zeolite Y, ZSM-12, MCM-22 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 h$^{-1}$, preferably of 1-10 h$^{-1}$ and a benzene/ethylene molar ratio of 3-10, preferably of 5-8.

Alternatively, the alkylation preferably comprises contacting the benzene in the presence of propylene with an alkylation catalyst under alkylation conditions to produce cumene, wherein said alkylation catalyst comprises a zeolite selected from the group consisting of beta zeolite, zeolite Y, ZSM-12, MCM-22 and mordenite and wherein said alkylation conditions comprise a temperature of 120-250° C. preferably of 150-230° C. a pressure of 1000-5000 kPa, preferably of 2500-3500 kPa, a Weight Hourly Space Velocity (WHSV) of 0.5-20 h$^{-1}$, preferably of 1-10 h$^{-1}$ and a benzene/propylene molar ratio of 3-10, preferably of 5-8.

Preferably, the stream rich in alkylated aromatic hydrocarbons is subjected to a separation to provide a monoalkylated aromatic product stream and stream comprising polyalkylated aromatic product stream and wherein said is recycled to the hydrocracking.

Preferably, the hydrocracking further produces C2-3 alkane that is subjected to olefins synthesis to provide C2-3 alkene that is subjected to alkylation as alkylation agent.

As used herein, the term "olefins synthesis" relates to a process for the conversion of alkanes to olefins. This term includes any process for the conversion of hydrocarbons to olefins including, but not limited to non-catalytic processes such as pyrolysis or steam cracking, catalytic processes such as propane dehydrogenation and combinations of the two such as catalytic steam cracking.

A very common process for olefins synthesis involves "steam cracking". As used herein, the term "steam cracking" relates to a petrochemical process in which saturated hydrocarbons are broken down into smaller, often unsaturated, hydrocarbons such as ethylene and propylene. In steam cracking gaseous hydrocarbon feeds like ethane and propane, or mixtures thereof (gas cracking) is diluted with steam and briefly heated in a furnace without the presence of oxygen. Typically, the reaction temperature is 750-900° C. and the reaction is only allowed to take place very briefly, usually with residence times of 50-1000 milliseconds. Preferably, a relatively low process pressure is to be selected of atmospheric up to 175 kPa gauge. Preferably, the hydrocarbon compounds ethane, propane and butanes are separately cracked in accordingly specialized furnaces to ensure cracking at optimal conditions. After the cracking temperature has been reached, the gas is quickly quenched to stop the reaction in a transfer line heat exchanger or inside a quenching header using quench oil. Steam cracking results in the slow deposition of coke, a form of carbon, on the reactor walls. Decoking requires the furnace to be isolated from the process and then a flow of steam or a steam/air mixture is passed through the furnace coils. This converts the hard solid carbon layer to carbon monoxide and carbon dioxide. Once this reaction is complete, the furnace is returned to service. The products produced by steam cracking depend on the composition of the feed, the hydrocarbon to steam ratio and on the cracking temperature and furnace residence time. Light hydrocarbon feeds such as ethane, propane, butane or light naphtha give product streams rich in the lighter polymer grade olefins, including ethylene, propylene, and butadiene.

To separate the different hydrocarbon compounds produced by steam cracking the cracked gas is subjected to a fractionation unit. The cracked gases may be subjected to multiple compression stages wherein a light distillate may be separated from the gases between the compression stages. Also acid gases ($CO_2$ and $H_2S$) may be removed between compression stages. In a following step, the gases produced by pyrolysis may be partially condensed over stages of a cascade refrigeration system to about where only the hydrogen remains in the gaseous phase. The different hydrocarbon compounds may subsequently be separated by simple distillation, wherein the ethylene, propylene and C4 olefins are the most important high-value chemicals produced by steam cracking. The methane produced by steam cracking is generally used as fuel gas, the hydrogen may be separated and recycled to processes that consume hydrogen, such as hydrocracking processes. The acetylene produced by steam cracking preferably is selectively hydrogenated to ethylene. The alkanes comprised in the cracked gas may be recycled to the process for olefins synthesis.

In case the C2-3 alkane is ethane, the olefins synthesis preferably is ethane cracking to provide the C2-3 alkene ethylene.

In case the C2-3 alkane is propane the olefins synthesis preferably is propane dehydrogenation to provide the C2-3 alkene propylene.

By converting the propane comprised in the LPG to propylene can be subjected to propane dehydrogenation to produce propylene and hydrogen, which is a much more carbon efficient method for producing olefins when compared to pyrolysis since in a propane dehydrogenation process, substantially no methane is produced.

By selecting olefins synthesis comprising propane dehydrogenation, the overall hydrogen balance of the integrated process can be improved. A further advantage of integrating dehydrogenation process into the process of the present invention is that a high-purity hydrogen stream is produced, which can be used as feed to hydrocracking without expensive purification.

The term "propane dehydrogenation" as used herein relates to a petrochemical process wherein a propane feedstream is converted into a product comprising propylene and hydrogen. Processes for the dehydrogenation of propane are well-known in the art and include oxidative dehydrogenation processes and non-oxidative dehydrogenation processes. In an oxidative dehydrogenation process, the process heat is provided by partial oxidation of the propane in the feed. In a non-oxidative dehydrogenation process, which is preferred in the context of the present invention, the process heat for the endothermic dehydrogenation reaction is provided by external heat sources such as hot flue gases obtained by burning of fuel gas or steam. In a non-oxidative dehydrogenation process the process conditions generally comprise a temperature of 540-700° C. and an absolute pressure of 25-500 kPa. For instance, the UOP Oleflex process allows for the dehydrogenation of propane to form propylene in the presence of a catalyst containing platinum supported on alumina in a moving bed reactor; see e.g. U.S. Pat. No. 4,827,072. The Uhde STAR process allows for the dehydrogenation of propane to form propylene or of butane to form butylene in the presence of a promoted platinum catalyst supported on a zinc-alumina spinel; see e.g. U.S. Pat. No. 4,926,005. The STAR process has been recently improved by applying the principle of oxydehydrogenation. In a secondary adiabatic zone in the reactor part of the hydrogen from the intermediate product is selectively converted with added oxygen to form water. This shifts the thermodynamic equilibrium to higher conversion and achieves a higher yield. Also the external heat required for the endothermic dehydrogenation reaction is partly supplied by the exothermic hydrogen conversion. The Lummus Catofin process employs a number of fixed bed reactors operating on a cyclical basis. The catalyst is activated alumina impregnated with 18-20 wt-% chromium; see e.g. EP 0 192 059 A1 and GB 2 162 082 A. The Catofin process has the advantage that it is robust and capable of handling impurities which would poison a platinum catalyst.

Accordingly, the dehydrogenation preferably comprises contacting the propane with a dehydrogenation catalyst under dehydrogenation conditions to produce propylene.

The dehydrogenation catalyst preferably comprises a catalyst support comprising 0.1-1 wt-% hydrogenation metal in relation to the total catalyst weight.

The dehydrogenation conditions preferably comprise a temperature of 450-800° C., preferably of 540-700° C. and a pressure of ambient to 1000 kPa gauge, preferably of 25-500 kPa gauge.

It is noted that the invention relates to all possible combinations of features described herein, particularly features recited in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

EXAMPLE 1

The main advantage of employing the hydrocracking process step in the process of the present invention is to produce high purity benzene, from a mixed C6 hydrocarbon stream, that is subsequently sent to alkylation unit for EB/cumene production. The results showed below were obtained by combination of laboratory experimentation and flowsheet modelling. The GHC product slate is simulated via a yield estimator that is based on extensive experimental data. The alkylation process step is modelled based on literature data published in Laredo et al. (2009) Applied Catalysis A: General 363, 11-18 and Laredo et al. (2009) Applied Catalysis A: General 363, 19-26.

The composition of reformate C6 cut can vary substantially but essentially consists of C6 paraffins, isoparaffins, benzene and small amount of naphthenes. Table 1 shows examples of reformate C6 cut contents:

TABLE 1

Examples of reformate C6 heart cut compositions:

| Component | RC6-1 (wt %) | RC6-2 (wt %) |
| --- | --- | --- |
| Benzene | 16.5 | 13.4 |
| Paraffins | 21.6 | 22.7 |
| Naphthenes | 4.9 | 4.6 |
| Iso-paraffins | 55.9 | 58.3 |

In example 1, RC6-2 is sent to the GHC unit that is operated at a temperature of 475° C., a hydrogen-to-hydrocarbon ratio of 3 and a pressure of 1379 kPa (200 psig) using a hydrocracking catalyst comprising a 1:1 weight ratio physical mixture of $Pt/Al_2O_3$ and ZSM-5 zeolite as described in Example 1 of WO/2013/182534 A1. The products of hydrocracking unit are divided into liquid aromatics (benzene and toluene) and lights gases (hydrogen, methane, ethane and propane).

A simple reactor model developed previously was used to predict the product slate of GHC unit. The reactor model uses correlations that was statistically obtained from experiments of wide range conditions, see Table 2. The model is capable of estimating the reaction products for a defined reactor feed composition and set of operating conditions.

TABLE 2

| Temperature (° C.) | 450 | 500 | 525 | 550 |
| Pressure (psig) | 100 | 200 | 300 | 400 |
| WHSV (hr$^{-1}$) | 2 | 3 | 4 | 4 |

Table 3 shows the product distribution after GHC unit. The high purity benzene produced by GHC is subsequently sent to an alkylation unit loaded with zeolite Beta (220° C., 3100-4800 kPa and benzene-to-olefin ratio of 1), where EB and cumene are produced with approximately 50% conversion (Laredo et al. (2009) loc. cit).

TABLE 3

Effluent of GHC unit using reformate C6 heart cut as feed:

| Component | Feed Composition (wt. %) | Effluent of GHC unit (wt. %) |
|---|---|---|
| Methane | — | 7.1 |
| Ethane | — | 13.6 |
| Propane | — | 65.1 |
| Benzene | 13.4 | 12.0 |
| Toluene | 0.9 | 1.6 |
| Cumene | — | 0.0 |
| Polyalkylbenzene | — | 0.0 |
| C6 iso-paraffins | 58.3 | 0.6 |
| C6 n-paraffins | 22.7 | — |
| C6 naphthenes | 4.6 | — |

For Example 1, the effluent of alkylation consists of 99.7% aromatics. Benzene recycle stream can be obtained by simple distillation.

EXAMPLE 2 (COMPARATIVE)

Example 2 is identical to the Example 1 except reformate C6 cut is sent directly to alkylation unit without pre-treated in the GHC unit. At the same alkylation conditions (220° C., 3.1-4.8 MPa and benzene-to-olefin ratio of 1), the following product distribution is predicted for both cases.

TABLE 4

Comparison of alkylation effluents in Examples 1 and 2:

| Component | Feed composition (wt. %) | Effluent of Alkylation unit (wt. %) Example 1: GHC + alkylation | Effluent of Alkylation unit (wt. %) Example 2: Direct alkylation |
|---|---|---|---|
| Methane | — | — | — |
| Ethane | — | — | — |
| Propane | — | — | — |
| Benzene | 13.4 | 49.3 | 6.4 |
| Toluene | 0.9 | — | 0.6 |
| Cumene | — | 38.0 | 5.5 |
| PAB | — | 11.0 | 2.8 |
| C6 iso-paraffins | 58.3 | 0.2 | 57 |
| C6 n-paraffins | 22.7 | — | 21.3 |
| C6 naphthenes | 4.6 | 0.1 | 4.1 |

For Example 2, the effluent of alkylation consists of 15.3% aromatics. Benzene needs to be recovered by extractive distillation or liquid-liquid extraction due to the unconverted C6 naphthenes, iso- and n-paraffin in the effluent.

The invention claimed is:

1. A process for producing alkylated aromatic hydrocarbons comprising:
   (a) subjecting a mixed hydrocarbon feedstream to a separation to provide a C6 cut;
   (b) subjecting the C6 cut to hydrocracking, wherein the hydrocracking comprises contacting the C6 cut with a hydrocracking catalyst comprising a hydrogenation metal and a zeolite under hydrocracking conditions comprising a temperature of 450-580° C., a pressure of 300-5000 kPa gauge, and a Weight Hourly Space Velocity of 0.1-20 h$^1$ to provide a benzene stream, wherein the benzene stream has a benzene purity of at least 98 wt %; and
   (c) subjecting the benzene stream to alkylation to provide a product stream rich in alkylated aromatic hydrocarbons.

2. The process according claim 1, wherein step (b) further comprises separating the benzene stream by vapor-liquid separation.

3. The process according to claim 1, wherein the hydrocracking catalyst comprises 0.1-1 wt-% of the hydrogenation metal in relation to the total catalyst weight and the zeolite has a pore size of 5-8 Å and a silica ($SiO_2$) to alumina ($Al_2O_3$) molar ratio of 5-200.

4. The process according to claim 3, wherein the benzene stream comprises less than 1 wt % co-boilers of benzene.

5. The process according to claim 1, wherein the hydrocracking produces a benzene stream comprises less than 1 wt % co-boilers of benzene.

6. The process according to claim 1, wherein the alkylation comprises contacting the benzene stream in the presence of ethylene with an alkylation catalyst under alkylation conditions to produce ethylbenzene, wherein said alkylation catalyst comprises beta zeolite, zeolite Y, ZSM-12, MCM-22 or mordenite and wherein said alkylation conditions comprise a temperature of 120-250° C., a pressure of 1000-5000 kPa, a Weight Hourly Space Velocity (WHSV) of 0.5-20 h$^{-1}$, and a benzene/ethylene molar ratio of 3-10.

7. The process according to claim 6, wherein the temperature is 150-230° C., the Weight Hourly Space Velocity is 1-10 h$^{-1}$, and the benzene/ethylene molar ratio is 5-8.

8. The process according to claim 1, wherein the alkylation comprises contacting the benzene stream in the presence of propylene with an alkylation catalyst under alkylation conditions to produce cumene, wherein said alkylation catalyst comprises a zeolite selected from the group consisting of beta zeolite, zeolite Y, ZSM-12, MCM-22 and mordenite and wherein said alkylation conditions comprise a temperature of 120-250° C., a pressure of 1000-5000 kPa, a Weight Hourly Space Velocity (WHSV) of 0.5-20 and a benzene/propylene molar ratio of 3-10.

9. The process according to claim 8, wherein the temperature is 150-230° C., the Weight Hourly Space Velocity is 1-10 h$^{-1}$, and the benzene/propylene molar ratio is 5-8.

10. The process according to claim 1, wherein the stream rich in alkylated aromatic hydrocarbons is subjected to a separation to provide a monoalkylated aromatic product stream and a stream comprising polyalkylated aromatic product and wherein said polyalkylated aromatic product is recycled to the hydrocracking.

11. The process according to claim 1, wherein the mixed hydrocarbon feedstream comprises reformate.

12. The process according to claim 1, the benzene stream has a benzene purity of greater than 99 wt %.

13. The process according to claim 1, wherein the hydrocracking further produces a C2-3 alkane stream that is subjected to olefins synthesis to provide a C2-3 alkene stream that is subjected to the alkylation as alkylation agent.

14. The process according to claim 13, wherein the C2-3 alkane stream comprises ethane and the olefins synthesis is ethane cracking to provide ethylene.

15. The process according to claim 13, wherein the C2-3 alkane stream comprises propane and the olefins synthesis is propane dehydrogenation to provide propylene.

16. The process according to claim 15, wherein the dehydrogenation comprises contacting the propane with a dehydrogenation catalyst under dehydrogenation conditions to produce propylene.

17. The process according to claim 16, wherein the dehydrogenation catalyst comprises a catalyst support comprising 0.1-1 wt-% hydrogenation metal in relation to the total catalyst weight.

18. The process according to claim 16, wherein the dehydrogenation conditions comprise a temperature of 450-800° C. and a pressure of ambient to 1000 kPa gauge.

19. The process according to claim 18, wherein the temperature is 540-700° C. and the pressure is 25-500 kPa gauge.

* * * * *